US008834378B2

(12) United States Patent
Addison et al.

(10) Patent No.: US 8,834,378 B2
(45) Date of Patent: Sep. 16, 2014

(54) SYSTEMS AND METHODS FOR DETERMINING RESPIRATORY EFFORT

(75) Inventors: Paul Stanley Addison, Midlothian (GB); James N. Watson, Fife (GB)

(73) Assignee: Nellcor Puritan Bennett Ireland, Galway (IE)

( * ) Notice: Subject to any disclaimer, the term of this patent is extended or adjusted under 35 U.S.C. 154(b) by 775 days.

(21) Appl. No.: 12/847,720

(22) Filed: Jul. 30, 2010

(65) Prior Publication Data
US 2012/0029361 A1 Feb. 2, 2012

(51) Int. Cl.
A61B 5/02 (2006.01)
A61B 5/0205 (2006.01)
A61B 5/08 (2006.01)
A61B 5/1455 (2006.01)
A61B 5/021 (2006.01)
A61B 5/00 (2006.01)

(52) U.S. Cl.
CPC ............. *A61B 5/0205* (2013.01); *A61B 5/7239* (2013.01); *A61B 5/0816* (2013.01); *A61B 5/14551* (2013.01); *A61B 5/02125* (2013.01); *A61B 5/02108* (2013.01)
USPC .......................................... 600/483; 600/500

(58) Field of Classification Search
USPC ......... 600/481, 483, 484, 508, 509, 513, 547; 607/17
See application file for complete search history.

(56) References Cited

U.S. PATENT DOCUMENTS

| | | | |
|---|---|---|---|
| 3,532,087 A | 10/1970 | Horn at al. | |
| 3,884,219 A | 5/1975 | Richardson et al. | |
| 3,926,177 A | 12/1975 | Hardway, Jr. et al. | |
| 4,289,141 A | 9/1981 | Cormier | |
| 4,696,307 A | 9/1987 | Montgieux | |
| 5,143,078 A | 9/1992 | Mather et al. | |
| 5,273,036 A | 12/1993 | Kronberg et al. | |
| 5,439,483 A | 8/1995 | Duong-Van | |
| 5,564,427 A * | 10/1996 | Aso et al. ...................... | 600/494 |
| 5,575,284 A | 11/1996 | Athan et al. | |
| 5,590,650 A | 1/1997 | Genova | |
| 5,632,272 A | 5/1997 | Diab et al. | |
| 5,680,871 A | 10/1997 | Ganshorn | |
| 5,682,898 A | 11/1997 | Aung et al. | |

(Continued)

FOREIGN PATENT DOCUMENTS

DE 10014077 A1 10/2001
JP 09084776 A 3/1997

(Continued)

OTHER PUBLICATIONS

DJ Pitson, A Sandell, R van den Hout and Stradling Jr, Use of pulse transit time as a measure of inspiratory effort in patients with obstructive sleep apnoea, 1995, European Respiratory Journal, vol. 8, pp. 1669-1674.*

(Continued)

*Primary Examiner* — Michael D'Angelo

(74) *Attorney, Agent, or Firm* — Shvarts & Leiz LLP

(57) ABSTRACT

Systems and methods for calculating a measure of respiratory effort of a subject are provided. The measure of respiratory effort may be calculated based on a differential pulse transit time (DPTT) calculated for received photoplethysmograph signals. The systems and methods may allow for the calculation of respiratory effort in absolute units, and without the need for calibrations from a device that measures blood pressure (e.g., a non-invasive blood pressure cuff).

19 Claims, 8 Drawing Sheets

(56) References Cited

U.S. PATENT DOCUMENTS

| | | |
|---|---|---|
| 5,778,881 A | 7/1998 | Sun et al. |
| 5,795,304 A | 8/1998 | Sun et al. |
| 5,797,840 A | 8/1998 | Akselrod et al. |
| 5,827,195 A | 10/1998 | Lander |
| 5,967,995 A | 10/1999 | Shusterman et al. |
| 5,980,463 A | 11/1999 | Brockway et al. |
| 6,002,952 A | 12/1999 | Diab et al. |
| 6,036,653 A | 3/2000 | Baba et al. |
| 6,094,592 A | 7/2000 | Yorkey et al. |
| 6,095,984 A | 8/2000 | Amano et al. |
| 6,117,075 A | 9/2000 | Barnea |
| 6,129,675 A | 10/2000 | Jay |
| 6,135,966 A | 10/2000 | Ko |
| 6,142,953 A | 11/2000 | Burton et al. |
| 6,171,257 B1 | 1/2001 | Weil et al. |
| 6,171,258 B1 | 1/2001 | Karakasoglu et al. |
| 6,208,951 B1 | 3/2001 | Kumar et al. |
| 6,293,915 B1 | 9/2001 | Amano et al. |
| 6,325,761 B1 | 12/2001 | Jay |
| 6,361,501 B1 | 3/2002 | Amano et al. |
| 6,363,270 B1 | 3/2002 | Colla et al. |
| 6,393,311 B1 | 5/2002 | Edgar, Jr. et al. |
| 6,398,727 B1 | 6/2002 | Bui et al. |
| 6,463,311 B1 | 10/2002 | Diab |
| 6,561,986 B2 | 5/2003 | Baura et al. |
| 6,599,251 B2 * | 7/2003 | Chen et al. ............... 600/485 |
| 6,606,511 B1 | 8/2003 | Ali et al. |
| 6,608,934 B2 | 8/2003 | Scheirer et al. |
| 6,654,623 B1 | 11/2003 | Kastle |
| 6,658,276 B2 | 12/2003 | Kianl et al. |
| 6,684,090 B2 | 1/2004 | Ali et al. |
| 6,702,752 B2 | 3/2004 | Dekker |
| 6,709,402 B2 | 3/2004 | Dekker |
| 6,748,252 B2 | 6/2004 | Lynn et al. |
| 6,801,798 B2 | 10/2004 | Geddes et al. |
| 6,810,277 B2 | 10/2004 | Edgar, Jr. et al. |
| 6,811,538 B2 | 11/2004 | Westbrook et al. |
| 6,896,661 B2 | 5/2005 | Dekker |
| 6,909,912 B2 | 6/2005 | Melker |
| 6,918,878 B2 | 7/2005 | Brodnick |
| 6,930,608 B2 | 8/2005 | Grajales et al. |
| 6,931,269 B2 | 8/2005 | Terry |
| 6,990,426 B2 | 1/2006 | Yoon et al. |
| 7,001,337 B2 | 2/2006 | Dekker |
| 7,020,507 B2 | 3/2006 | Scharf et al. |
| 7,024,235 B2 | 4/2006 | Melker et al. |
| 7,025,730 B2 | 4/2006 | Cho et al. |
| 7,035,679 B2 | 4/2006 | Addison et al. |
| 7,043,293 B1 | 5/2006 | Baura |
| 7,052,469 B2 | 5/2006 | Minamiura et al. |
| 7,054,453 B2 | 5/2006 | Causevic et al. |
| 7,054,454 B2 | 5/2006 | Causevic et al. |
| 7,079,888 B2 | 7/2006 | Oung et al. |
| 7,171,251 B2 | 1/2007 | Sarussi et al. |
| 7,171,269 B1 | 1/2007 | Addison et al. |
| 7,173,525 B2 | 2/2007 | Albert |
| 7,203,267 B2 | 4/2007 | De Man et al. |
| 7,225,013 B2 | 5/2007 | Geva et al. |
| 7,246,618 B2 | 7/2007 | Habashi |
| 7,254,500 B2 | 8/2007 | Makeig et al. |
| 7,289,835 B2 | 10/2007 | Mansfield et al. |
| 7,309,314 B2 | 12/2007 | Grant et al. |
| 7,344,497 B2 | 3/2008 | Kline |
| 7,381,185 B2 | 6/2008 | Zhirnov et al. |
| 7,390,300 B2 * | 6/2008 | Inukai et al. ............... 600/485 |
| 7,398,115 B2 | 7/2008 | Lynn |
| 7,421,296 B1 | 9/2008 | Benser et al. |
| 7,425,201 B2 | 9/2008 | Euliano et al. |
| 7,515,949 B2 | 4/2009 | Norris |
| 7,519,488 B2 | 4/2009 | Fu et al. |
| 7,523,011 B2 | 4/2009 | Akiyama et al. |
| 2003/0163057 A1 | 8/2003 | Flick et al. |
| 2005/0022606 A1 | 2/2005 | Partin et al. |
| 2005/0043616 A1 | 2/2005 | Chinchoy |
| 2005/0109340 A1 | 5/2005 | Tehrani |
| 2005/0215915 A1 | 9/2005 | Noda et al. |
| 2005/0222502 A1 | 10/2005 | Cooper |
| 2005/0251056 A1 | 11/2005 | Gribkov et al. |
| 2006/0074333 A1 | 4/2006 | Huiku |
| 2006/0155206 A1 | 7/2006 | Lynn |
| 2006/0173257 A1 | 8/2006 | Nagai et al. |
| 2006/0209631 A1 | 9/2006 | Melese et al. |
| 2006/0211930 A1 | 9/2006 | Scharf et al. |
| 2006/0217603 A1 | 9/2006 | Nagai et al. |
| 2006/0229519 A1 | 10/2006 | Fujiwara et al. |
| 2006/0241506 A1 | 10/2006 | Melker et al. |
| 2006/0258921 A1 | 11/2006 | Addison et al. |
| 2006/0265022 A1 | 11/2006 | John et al. |
| 2006/0282001 A1 | 12/2006 | Noel et al. |
| 2007/0015976 A1 | 1/2007 | Miesel et al. |
| 2007/0021673 A1 | 1/2007 | Arbel et al. |
| 2007/0027375 A1 | 2/2007 | Melker et al. |
| 2007/0062531 A1 | 3/2007 | Fisher et al. |
| 2007/0073120 A1 | 3/2007 | Li et al. |
| 2007/0073124 A1 | 3/2007 | Li et al. |
| 2007/0129647 A1 | 6/2007 | Lynn |
| 2007/0149883 A1 | 6/2007 | Yesha |
| 2007/0167694 A1 | 7/2007 | Causevic et al. |
| 2007/0167851 A1 | 7/2007 | Vitali et al. |
| 2007/0219059 A1 | 9/2007 | Schwartz et al. |
| 2007/0282212 A1 | 12/2007 | Sierra et al. |
| 2008/0045832 A1 | 2/2008 | McGrath |
| 2008/0060138 A1 | 3/2008 | Price et al. |
| 2008/0066753 A1 | 3/2008 | Martin et al. |
| 2008/0076992 A1 | 3/2008 | Hete et al. |
| 2008/0082018 A1 | 4/2008 | Sackner et al. |
| 2008/0092898 A1 | 4/2008 | Schneider et al. |
| 2008/0119756 A1 | 5/2008 | Wada |
| 2008/0171946 A1 | 7/2008 | Hansmann |
| 2008/0190430 A1 | 8/2008 | Melker et al. |
| 2008/0202525 A1 | 8/2008 | Mitton et al. |
| 2008/0214903 A1 | 9/2008 | Orbach |
| 2008/0243021 A1 | 10/2008 | Causevic et al. |
| 2009/0326386 A1 | 12/2009 | Sethi et al. |
| 2009/0326393 A1 | 12/2009 | Sethi et al. |
| 2009/0326402 A1 | 12/2009 | Addison et al. |
| 2010/0016692 A1 * | 1/2010 | Addison et al. ............... 600/324 |
| 2010/0312075 A1 | 12/2010 | McGonigle et al. |
| 2010/0331715 A1 | 12/2010 | Addison et al. |
| 2010/0331716 A1 | 12/2010 | Watson et al. |
| 2011/0004081 A1 | 1/2011 | Addison et al. |
| 2011/0021892 A1 | 1/2011 | Addison et al. |
| 2011/0028802 A1 | 2/2011 | Addison et al. |
| 2011/0071406 A1 | 3/2011 | Addison et al. |

FOREIGN PATENT DOCUMENTS

| | | |
|---|---|---|
| WO | WO-00/21438 | 4/2000 |
| WO | WO-01/25802 | 4/2001 |
| WO | WO-01/62152 | 8/2001 |
| WO | WO-01/76471 | 10/2001 |
| WO | WO-03000125 | 1/2003 |
| WO | WO-03/055395 | 7/2003 |
| WO | WO-2004/075746 | 9/2004 |
| WO | WO-2004/105601 | 12/2004 |
| WO | WO-2005/096170 | 10/2005 |
| WO | WO-2006/085120 | 8/2006 |
| WO | WO-2008/043864 | 4/2008 |

OTHER PUBLICATIONS

Y.M. Wong and Y. T. Zhang, The Effects of Exercises on the Relationship between Pulse Transit Time and Arterial Blood Pressure, 2005, Engineering in Medicine and Biology Society, pp. 5576-5578.*

Chua et al., "Pulse transit time-derived respiratory parameters and their variability across sleep stages." Engineering in Medicine and Biology Society, 2005. 27th Annual Conference, Shanghai, China, pp. 6153-6156 (Sep. 1-4, 2005).

Addison, Paul S., The Illustrated Wavelet Transform Handbook, Taylor & Francis Group, 2002.

Addison, Paul, "The Little Wave with the Big Future," Physics World, Mar. 2004, pp. 35-39.

(56) References Cited

OTHER PUBLICATIONS

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, 2006.

Leonard, Paul A., Clifton, David, Addison, Paul S., Watson, James N., Beattie, Tom "An Automated Algorithm for Determining Respiratory Rate by Photoplethysmogram in Children," Acta Paediatricia, 2006; 95: 1124-1128.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Yamada, Michio, "Wavelet Analysis and Its Application," Journal of the Institute of Electronics, Information and Communication Engineers, vol. 76, No. 5, May 1993, pp. 518-528.

U.S. Appl. No. 61/369,452, filed Jul. 30, 2010.

* cited by examiner

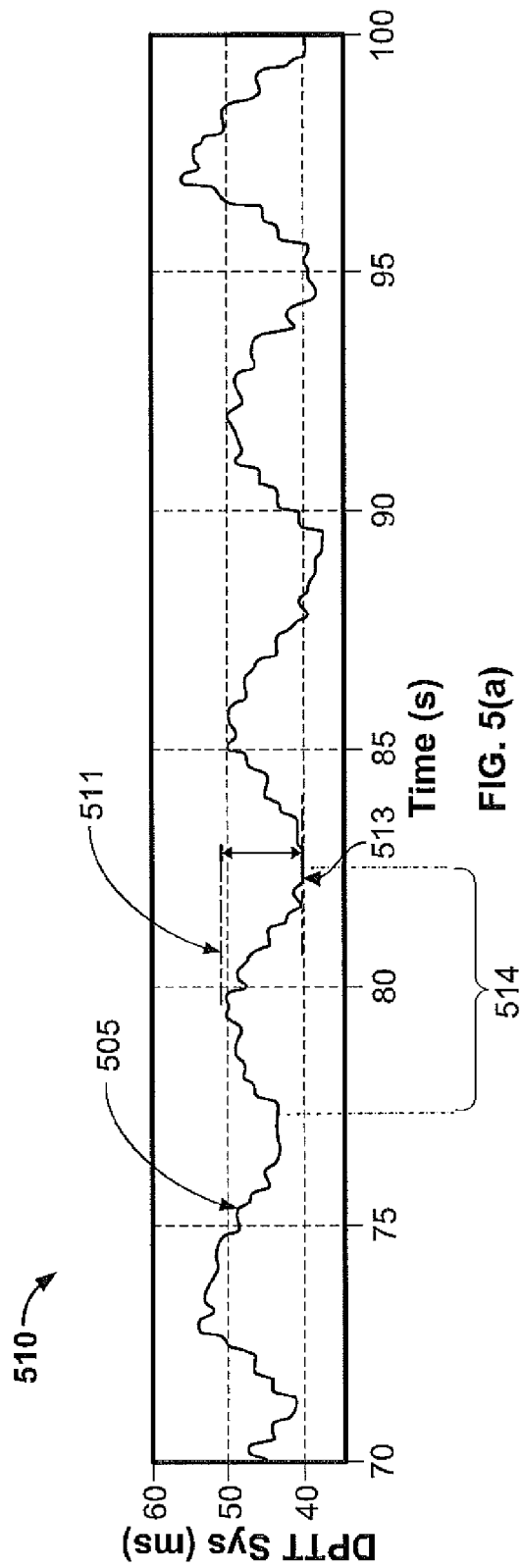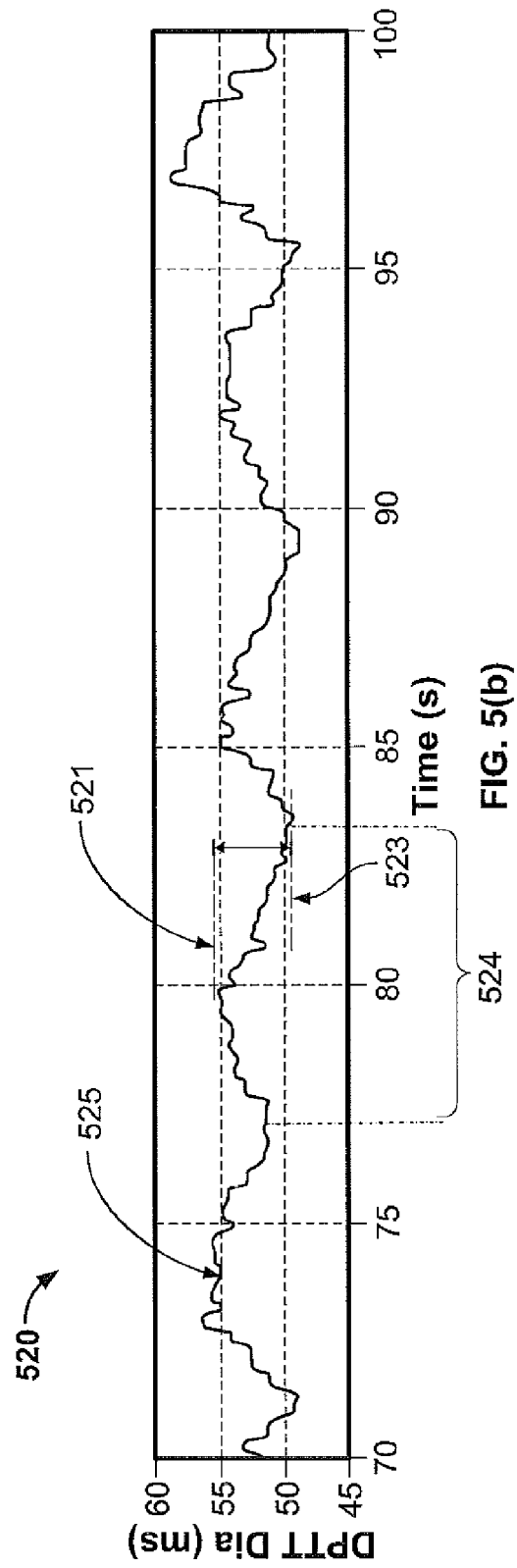

US 8,834,378 B2

SYSTEMS AND METHODS FOR DETERMINING RESPIRATORY EFFORT

SUMMARY

Continuous non-invasive blood pressure (CNIBP) monitoring systems allow a patient's blood pressure to be tracked continuously, unlike standard occlusion cuff techniques, and without the hazards of invasive arterial lines. Some such systems use multiple pulse oximetry sensors located to measure photoplethysmograph (PPG) signals at multiple body sites on a patient. The resulting multiple PPG signals may be compared against each other to estimate the patient's blood pressure. Chen et al. U.S. Pat. No. 6,599,251, which is hereby incorporated by reference herein in its entirety, discloses some techniques for continuous and non-invasive blood pressure monitoring using two probes or sensors that may be used in conjunction with the present disclosure.

A differential pulse transit time (DPTT) may be determined based on the received PPG signals, A DPTT may represent the difference in the arrival times of a portion of a cardiac wave between the two locations, and may be determined based on identifying a corresponding fiducial point in each of the two PPG signals (e.g., a maximum, minimum, or a notch).

The respiratory effort of a patient may be determined based on DPTTs and relying upon a blood pressure calibration measurement from a patient using additional equipment, such as a non-invasive blood pressure cuff. These calibrations may not be practical for a patient who has a limited range of motion, or who is not able to accommodate the cuff. In addition, these calibrations may be compromised because the patient is aware that he or she is being monitored. Accordingly, techniques that allow for the measurement of respiratory effort without such calibration measurements are needed.

In an embodiment, respiratory effort may be determined based on characteristic points of DPTT signals—e.g., the maximum and minimum DPTT values over a single respiration cycle, or any suitable window of time. The difference between the maximum and minimum DPTT values may then be used to determine the change in blood pressure of a patient. Calculated changes in diastolic and systolic blood pressure measurements may be used in combination to obtain a change in mean arterial pressure. In another embodiment, one or more mean DPTT measurements may be calculated and used to determine a change in blood pressure over particular periods of time For example, an increase in the baseline (i.e., mean DPTT) of a DPTT signal over time may indicate increased autonomic and/or respiratory activity on behalf of the patient being monitored, and thus an increase in the patient's blood pressure.

BRIEF DESCRIPTION OF THE DRAWINGS

The above and other features of the present disclosure, its nature and various advantages will be more apparent upon consideration of the following detailed description, taken in conjunction with the accompanying drawings and in which:

FIGS. 5(a) and 5(b) show illustrative plots of DPTT measurements in accordance with embodiments of the disclosure;

DETAILED DESCRIPTION

Some CNIBP monitoring techniques utilize two probes or sensors positioned at two different locations on a subject's body. The elapsed time, T, between the arrivals of corresponding points of a pulse signal at the two locations may then be determined using signals obtained by the two probes or sensors. The estimated blood pressure, p, may then be related to the elapsed time, T, by $$p = a + b \cdot \ln(T) \quad (1)$$

where a and b are constants that may be dependent upon the nature of the subject and the nature of the signal detecting devices. Other suitable equations using an elapsed time between corresponding points of a pulse signal may also be used to derive an estimated blood pressure measurement.

Equation (1) may be used to determine the estimated blood pressure from the time difference, T, between corresponding points of a pulse signal received by two sensors or probes attached to two different locations of a subject. As described in more detail below, however, the value used for the time difference, T, in equation (1) (or in any other blood pressure equation using an elapsed time value between corresponding points of a pulse signal) may also be derived from a signal obtained from a single sensor or probe. In one suitable approach, the signal obtained from the single sensor or probe may take the form of a PPG signal obtained, for example, from a CNIBP monitoring system or pulse oximeter.

A PPG signal may be used to determine blood pressure according to the present disclosure at least in part because the shape of the PPG signal may be considered to be made up of the pulse wave and its many reflections throughout the circulatory system. As such, blood pressure equations used in continuous blood pressure monitoring techniques that use sensors or probes at two locations (e.g., equation (1) above) may also be used with continuous blood pressure monitoring techniques that use only a single probe. As described in more detail below, characteristic points may be identified in a detected PPG signal. To determine blood pressure using a PPG signal, the time difference, T, in equation (1) (or in any other blood pressure equation using the time between corresponding points of a pulse signal) may then be substituted with the time between two characteristic points in a detected PPG signal.

Figure 1:
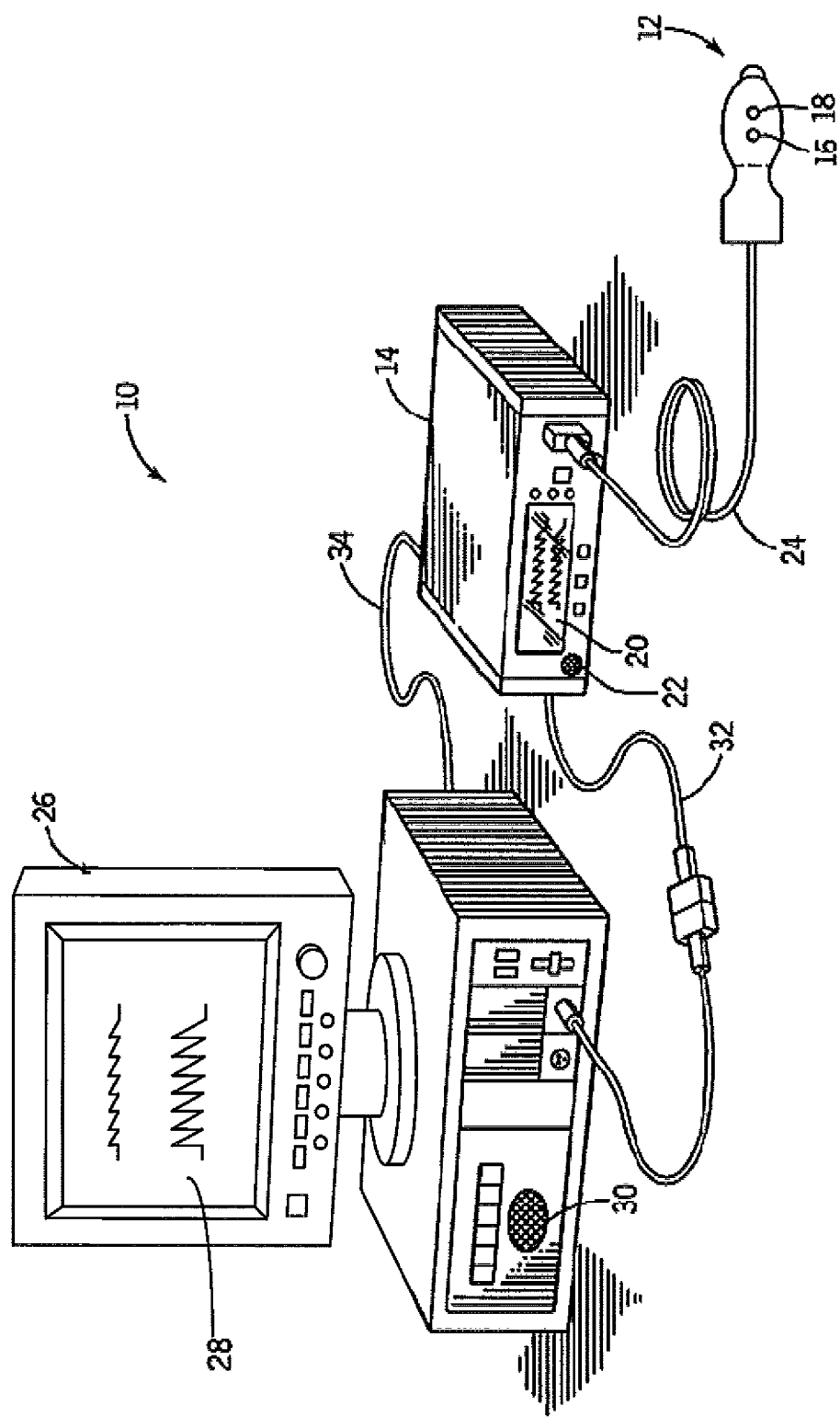
FIG. 1 shows an illustrative pulse oximetry system in accordance with an embodiment.

FIG. 1 is a perspective view of an embodiment of a CNIBP monitoring system 10 that may also be used to perform pulse oximetry. System 10 may include a sensor 12 and a monitor 14. Sensor 12 may include an emitter 16 for emitting light at one or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, detector 18 (e.g., a reflective sensor) may be positioned anywhere a strong pulsatile flow may be detected (e.g., over arteries in the neck, wrist, thigh, ankle, ear, or any other suitable location). In an embodiment, emitter 16 and detector 18 may be arranged so that light from emitter 16 penetrates the tissue and is reflected by the tissue into detector 18, such as a sensor designed to obtain pulse oximetry or CNIBP data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters (e.g., blood pressure) based at least in part on data received from sensor 12 relating to light emission and detection. In an alternative embodiment, the calculations may be performed on the monitoring device itself and the result of the light intensity reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multi-parameter patient monitor 26 may be configured to display an estimate of a patient's blood pressure from monitor 14, blood oxygen saturation generated by monitor 14 (referred to as an "$SpO_2$" measurement), and pulse rate information from monitor 14.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown), Monitor 14 may be powered by a battery (not shown) or by a conventional power source such as a wall outlet.

Calibration device 80, which may be powered by monitor 14, a battery, or by a conventional power source such as a wall outlet, may include any suitable blood pressure calibration device. For example, calibration device 80 may take the form of any invasive or non-invasive blood pressure monitoring or measuring system used to generate reference blood pressure measurements for use in calibrating the CNIBP monitoring techniques described herein. Such calibration devices may include, for example, an aneroid or mercury sphygmomanometer and occluding cuff, a pressure sensor inserted directly into a suitable artery of a patient, an oscillometric device or any other device or mechanism used to sense, measure, determine, or derive a reference blood pressure measurement. In one suitable approach, calibration device 80 may include a manual input device (not shown) used by an operator to manually input reference blood pressure measurements obtained from some other source (e.g., an external invasive or non-invasive blood pressure measurement system).

Calibration device 80 may also access reference blood pressure measurements stored in memory (e.g., RAM, ROM, or a storage device). For example, in one suitable approach, calibration device 80 may access reference blood pressure measurements from a relational database stored within calibration device 80, monitor 14, or multi-parameter patient monitor 26. As described in more detail below, the reference blood pressure measurements generated or accessed by calibration device 80 may be updated in real-time, resulting in a continuous source of reference blood pressure measurements for use in continuous or periodic calibration. Alternatively, reference blood pressure measurements generated or accessed by calibration device 80 may be updated periodically, and calibration may be performed on the same periodic cycle. In the depicted embodiments, calibration device 80 is connected to monitor 14 via cable 82. In other embodiments, calibration device 80 may be a stand-alone device that may be in wireless communication with monitor 14. Reference blood pressure measurements may then be wirelessly transmitted to monitor 14 for use in calibration. In still other embodiments, calibration device 80 is completely integrated within monitor 14. Alternative, in other embodiments, calibration device 80 is omitted from CNIBP monitoring system 10.

Figure 2:
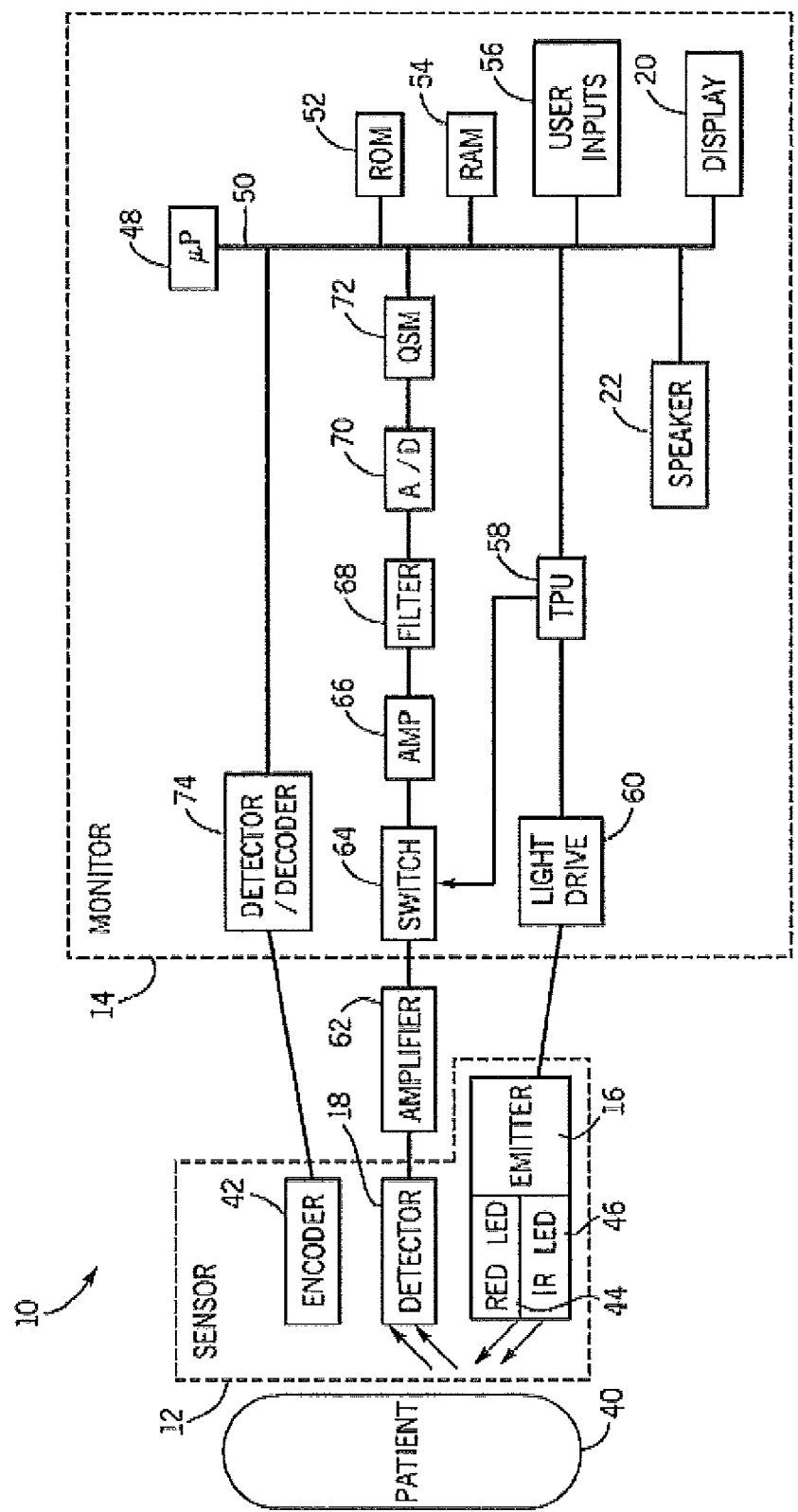
FIG. 2 is a block diagram of the illustrative pulse oximetry system of FIG. 1 coupled to a patient in accordance with an embodiment.

FIG. 2 is a block diagram of a CNIBP monitoring system, such as system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least one wavelength of light (e.g., RED or IR) into a patient's tissue 40. For calculating $SpO_2$, emitter 16 may include a RED light emitting light source such as RED light emitting diode (LED) 44 and an IR light emitting light source such as IR LED 46 for emitting light into the patient's tissue 40. In other embodiments, emitter 16 may include a light emitting light source of a wavelength other than RED or IR. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the emitted wavelengths (or any other suitable wavelength). Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed, reflected or scattered, less light of that wavelength is received from the tissue by the detector 18. After converting the received light to an electrical signal, detector 18 may send the signal to monitor 14, where physiological parameters may be calculated based on the absorption of one or more of the RED and IR (or other suitable) wavelengths in the patient's tissue 40.

In an embodiment, encoder 42 may contain information about sensor 12, such as what type of sensor it is (e.g., whether the sensor is intended for placement on a forehead or digit) and the wavelength or wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms, Encoder 42 may, for instance, be a coded resistor which stores values corresponding to the type of sensor 12 or the type of each sensor in the sensor array, the wavelength or wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelength or wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50, Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as blood pressure, $SpO_2$, and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the sensor or probe is attached.

Noise (e.g., from patient movement) can degrade a CNIBP or pulse oximetry signal relied upon by a physician, without the physician's awareness. This is especially true if the monitoring of the patient is remote, the motion is too small to be observed, or the doctor is watching the instrument or other parts of the patient, and not the sensor site. Processing CNIBP or pulse oximetry (i.e., PPG) signals may involve operations that reduce the amount of noise present in the signals or otherwise identify noise components in order to prevent them from affecting measurements of physiological parameters derived from the PPG signals.

CNIBP monitoring system 10 may also include calibration device 80. Although shown external to monitor 14 in the example of FIG. 2, calibration device 80 may additionally or alternatively be internal to monitor 14. Calibration device 80 may be connected to internal bus 50 of monitor 14. As described in more detail below, reference blood pressure measurements from calibration device 80 may be accessed by microprocessor 48 for use in calibrating the CNIBP measurements.

Figure 3:
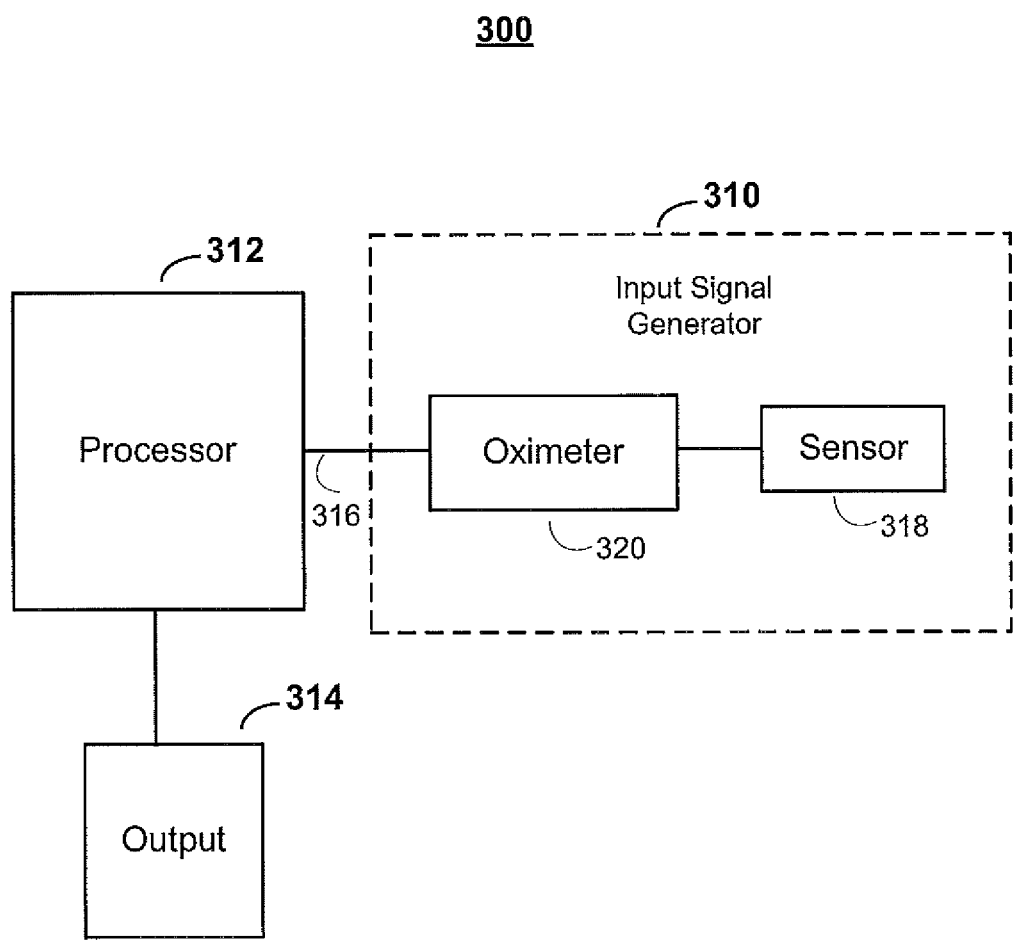
FIG. 3 is an illustrative processing system in accordance with an embodiment.

FIG. 3 is an illustrative processing system 300 in accordance with an embodiment. In an embodiment, input signal generator 310 generates an input signal 316. As illustrated, input signal generator 310 may include oximeter 320 (or similar device) coupled to sensor 318, which may provide as input signal 316, a PPG signal. It will be understood that input signal generator 310 may include any suitable signal source, signal generating data, signal generating equipment, or any combination thereof to produce signal 316.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

In an embodiment, signal 316 may be coupled to processor 312. Processor 312 may be any suitable software, firmware, and/or hardware, and/or combinations thereof for processing signal 316. For example, processor 312 may include one or more hardware processors (e.g., integrated circuits), one or more software modules, computer-readable media such as memory, firmware, or any combination thereof. Processor 312 may, for example, be a computer or may be one or more chips (i.e., integrated circuits). Processor 312 may perform some or all of the calculations associated with the blood pressure monitoring methods of the present disclosure. For example, processor 312 may determine the time difference, T, between any two chosen characteristic points of a PPG signal obtained from input signal generator 310. Processor 312 may also be configured to apply equation (1) (or any other blood pressure equation using an elapsed time value) and compute estimated blood pressure measurements on a continuous or periodic basis. Processor 312 may also perform any suitable signal processing of signal 316 to filter signal 316, such as any suitable band-pass filtering, adaptive filtering, closed-loop filtering, and/or any other suitable filtering, and/or any combination thereof. For example, signal 316 may be filtered one or more times prior to or after identifying characteristic points in signal 316.

Processor 312 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. Processor 312 may be coupled to a calibration device (not shown) that may generate or receive as input reference blood pressure measurements for use in calibrating CNIBP calculations.

Processor 312 may be coupled to output 314. Output 314 may be any suitable output device such as, for example, one or more medical devices (e.g., a medical monitor that displays various physiological parameters, a medical alarm, or any other suitable medical device that either displays physiological parameters or uses the output of processor 212 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 300 may be incorporated into system 10 (FIGS. 1 and 2) in which, for example, input signal generator 310 may be implemented as parts of sensor 12 and monitor 14 and processor 312 may be implemented as part of monitor 14. In one suitable approach, portions of system 300 may be configured to be portable. For example, all or a part of system 300 may be embedded in a small, compact object carried with or attached to the patient (e.g., a watch (or other piece of jewelry) or cellular telephone). In such embodiments, a wireless transceiver (not shown) may also be included in system 300 to enable wireless communication with other components of system 10. As such, system 10 may be part of a fully portable and continuous blood pressure monitoring solution.

According to the present disclosure, reliable blood pressure measurements may be derived from a PPG signal obtained from a single sensor or probe. In one suitable approach, the constants a and b in equation (1) above may be determined by performing a calibration. The calibration may involve taking a reference blood pressure reading to obtain a reference blood pressure $P_0$, measuring the elapsed time $T_0$ corresponding to the reference blood pressure, and then determining values for both of the constants a and b from the reference blood pressure and elapsed time measurement. Calibration may be performed at any suitable time (e.g., once initially after monitoring begins) or on any suitable schedule (e.g., a periodic or event-driven schedule). In one suitable approach, constants a and b in equation (1) above may be predetermined—for example, determined based on empirical data without performing a calibration.

In one suitable approach, the calibration may include performing calculations mathematically equivalent to $$a = c_1 + \frac{c_2(P_0 - c_1)}{\ln(T_0) + c_2} \tag{2}$$

and $$b = \frac{P_0 - c_1}{\ln(T_0) + c_2} \tag{3}$$

to obtain values for the constants a and b, where $c_1$ and $c_2$ are predetermined constants that may be determined, for example, based on empirical data.

In other embodiments, determining the plurality of constant parameters in the multi-parameter equation (1) may include performing calculations mathematically equivalent to $$a = P_0 - (c_3 T_0 + c_4) \ln(T_0) \quad (4)$$

and $$b = c_3 T_0 + c_4 \quad (5)$$

where a and b are first and second parameters and $c_3$ and $c_4$ are predetermined constants that may be determined, for example, based on empirical data.

In one suitable approach, the multi-parameter equation (1) may include a non-linear function which is monotonically decreasing and concave upward in a manner specified by the constant parameters.

As mentioned above, multi-parameter equation (1) may be used to determine estimated blood pressure measurements from the time difference, T, between two or more characteristic points of a PPG signal. In one suitable approach, the PPG signals used in the CNIBP monitoring techniques described herein are generated by a pulse oximeter or similar device.

The present disclosure may be applied to measuring systolic blood pressure, diastolic blood pressure, mean arterial pressure (MAP), or any combination of the foregoing on an on-going, continuous, or periodic basis. In one suitable approach, measuring the time difference, T, includes measuring a first time difference, $T_s$, for certain portions (i.e., portions corresponding generally to the parts of the signals associated with systolic blood pressure) of the PPG signal. Measuring the first time difference may comprise maximizing a cross-correlation between some components of the PPG signal. In such measurements, portions of the PPG signal that fall below a first threshold may not be considered in one suitable approach. The first threshold may be an average value for the signal (or equivalently a mean value for the signal).

Figure 4:
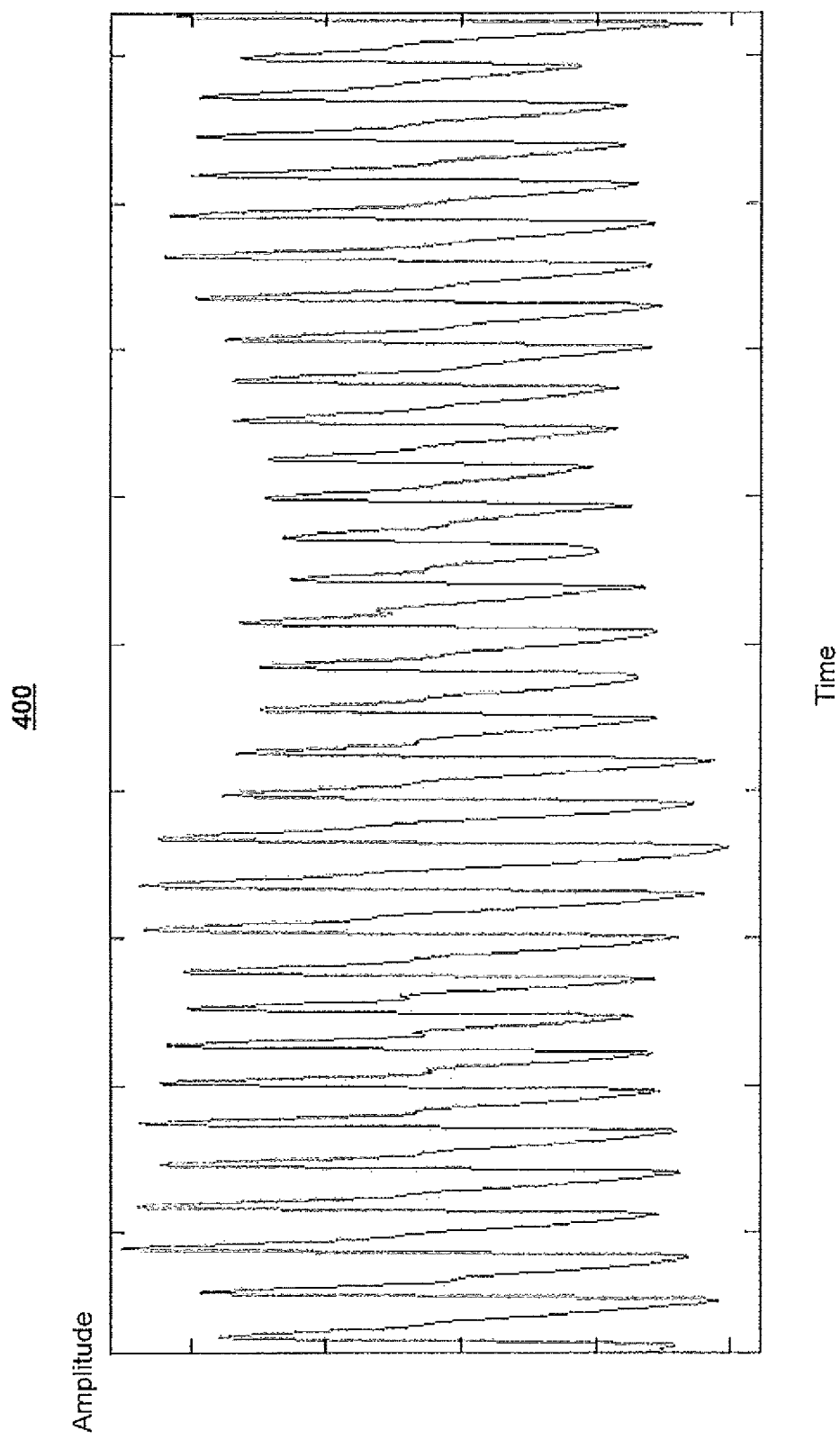
FIG. 4 shows an illustrative PPG signal in accordance with an embodiment.

FIG. 4 shows illustrative PPG signal 400. As described above, in one suitable approach PPG signal 400 may be generated by a pulse oximeter or similar device positioned at any suitable location of a subject's body. Notably, PPG signal 400 may be generated using only a single sensor or probe attached to the subject's body. Such techniques are described with respect to U.S. patent application Ser. No. 12/242,238, filed on Sep. 30, 2008, entitled "Systems and Methods for Non-Invasive Blood Pressure Monitoring" and U.S. patent application Ser. No. 12/242,867, filed on Sep. 30, 2008, entitled "Systems And Methods For Non-Invasive Continuous Blood Pressure Determination," which are both hereby incorporated by reference herein in their entireties.

Characteristic points in a PPG (e.g., PPG signal 400) may be identified in a number of ways. For example, in one suitable approach, the turning points of 1st, 2nd, 3rd (or any other) derivative of the PPG signal are used as characteristic points. Additionally or alternatively, points of inflection in the PPG signal (or any suitable derivative thereof) may also be used as characteristic points of the PPG signal. The time difference, T, may correspond to the time it takes the pulse wave to travel a predetermined distance (e.g., a distance from the sensor or probe to a reflection point and back to the sensor or probe). Characteristic points in the PPG signal may also include the time between various peaks in the PPG signal and/or in some derivative of the PPG signal. For example, in one suitable approach, the time difference, T, may be calculated between (1) the maximum peak of the PPG signal in the time domain and the second peak in the 2nd derivative of the PPG signal (the first 2nd derivative peak may be close to the maximum peak in the time domain) and/or (2) peaks in the 2nd derivative of the PPG signal. Any other suitable time difference between any suitable characteristic points in the PPG signal (e.g., PPG signal 400) or any derivative of the PPG signal may be used as T in other embodiments.

In one suitable approach, the time difference between the adjacent peaks in PPG signals, the time difference between the adjacent valleys in PPG signals, or the time difference between any combination of peaks and valleys, can be used as the time difference T. As such, adjacent peaks and/or adjacent valleys in PPG signals (or in any derivative thereof) may also be considered characteristics points. In one suitable approach, these time differences may be divided by the actual or estimated heart rate to normalize the time differences. In one suitable approach, the resulting time difference values between two peaks may be used to determine the systolic blood pressure, and the resulting time difference values between two valleys may be used to determine the diastolic blood pressure. In an embodiment, the time differences between characteristic points associated with a pulse's maximal and minimal turning points (i.e., those characteristic points associated with maximum and minimum pressures) may be measured from relatively stable points in PPG signals.

A patient's blood pressure may be monitored continuously using moving PPG signals. PPG signal detection means may include a pulse oximeter (or other similar device) and associated hardware, software, or both. A processor may continuously analyze the signal from the PPG signal detection means in order to continuously monitor a patient's blood pressure.

In one suitable approach, past blood pressure measurements are used to scale current and future measurements. For example, to avoid large swings in detected blood pressure a running or moving blood pressure average may be maintained. Detected blood pressure values outside some predefined threshold of the moving average may be ignored in one suitable approach. Additionally or alternatively, detected blood pressure values outside some pre-defined threshold of the moving average may automatically signal a recalibration event.

According to one suitable approach, one or more calibration (or recalibration) steps may be employed by measuring the patient's blood pressure (or a reference blood pressure), $P_0$, and then measuring the corresponding elapsed time, $T_0$, between the chosen characteristic points in the PPG signal. Updated or refined values for constants a and b of equation (1) (or other suitable blood pressure equation) may then be computed based on the calibration. Calibration may be performed once, initially at the start of the continuous monitoring, or calibration may be performed on a regular or event-driven schedule. In one suitable approach, calibration may also include changing the characteristic points used to compute the time difference, T. For example, several different blood pressure determinations may be made in parallel using different sets of characteristic points. The set of characteristic points that yields the most accurate blood pressure reading during the calibration period may then be used as the new set of characteristic points. As such, the characteristic points of the PPG signal used in the blood pressure determination may be modified on-the-fly and may vary during a single monitoring session. Such an adaptive approach to selecting characteristic points in the PPG signal may help yield more accurate blood pressure readings. In other embodiments, no calibration steps are performed in order to yield accurate blood pressure measurements, as will be described below.

In one suitable approach, no calibration steps are performed in order to yield accurate blood pressure measurements. It may be important to monitor certain physiological parameters of a patient, such as respiration rate and blood pressure, in a clinical setting. For example, blood pressure information may be important for diagnosing or monitoring a cardiovascular ailment. However, blood pressure measurements need not rely on an initial calibration measurement taken by additional equipment, such as a non-invasive blood pressure cuff, as will be described with respect to the embodiments that follow.

In an embodiment, a blood pressure measurement may be obtained based on a localized change in a related indicator, such as differential pulse transit time (DPTT). These changes in DPTT may directly translate into changes in blood pressure and may be used to generate CNIPB readings. In one suitable approach, the blood pressure measurement may be provided in absolute units of pressure (e.g., mmHG or $cmH_2O$). Such a measurement may be more convenient for clinicians and/or more useful in further calculations by monitoring equipment. As discussed above, no blood pressure measurement device (e.g., a non-invasive blood pressure cuff) may be required to obtain a measure of blood pressure from an initial calibration measurement. The only probes that may be required for the measurement of blood pressure fluctuations due to respiration are one or more oximeter probes attached to one or more sites on the body of the patient at particular distances from the heart (e.g., at the finger and/or the forehead). Such probes may be substantially similar to sensor 12 (FIG. 1). In one suitable approach, respiratory effort may be determined from the changes in DPTT. Although the present disclosure will be described with respect to the measurement of respiratory effort (e.g., as derived from changes in blood pressure), it will be understood that the present disclosure may be applied to any suitable physiological parameter (e.g., respiration rate, blood oxygen saturation) and may be used to determine a characteristic value of that physiological parameter. Embodiments will now be discussed in connection with FIGS. 5-9.

The respiratory effort of a patient may be derived from any suitable received signal or signals using, for example, system 10 or system 400. FIGS. 5(a), 5(b), 6, and 7 show illustrative plots 510, 520, 600, and 700 of DPTT measurements in accordance with embodiments of the disclosure. In one suitable approach, plots 510, 520, 600, and 700 may be produced from data gathered from an individual probe or sensor (i.e., sensor 12) used with a detector (i.e., detector 18) suitably positioned anywhere on patient 40 (e.g., in an area where a strong pulsatile flow may be detected, such as over arteries in the neck, wrist, thigh, ankle, ear, or any other suitable location).

In addition, in one suitable approach the data may be gathered while the patient is breathing against a slight resistance in order to cause more pronounced changes in DPTT within a respiratory cycle. These pronounced changes are then used to determine relative changes in blood pressure. The data may be captured in a PPG signal, which may then be analyzed (i.e., using processor 412) and used to compute DPTT measurements. As shown in plots 510 and 520, the DPTT measurements may be plotted over time, with DPTT measurements from diastolic and systolic periods of a heart beat each plotted separately. These sets of DPTT measurements may be referred to as "systolic DPTT measurements" and "diastolic DPTT measurements", respectively. In one suitable approach (not shown), DPTT measurements may be related to thoracic pressure changes. In one suitable approach, these plots may contain continuous representations (e.g., signals) of DPTT measurements over time. For example, plot 510 depicts systolic DPTT measurements as signal 505, and plot 520 depicts diastolic DPTT measurements as signal 525. In addition, plots 600 and 700 depict diastolic or systolic DPTT measurements as signals 610 and 702, respectively.

In one suitable approach, signals 505, 525, 610, and 702 may be modulated based on a patient's breathing (e.g., the baseline of signals 505, 525, 610, and 702 may oscillate in relation to the patient's breathing) and may include other oscillatory features (e.g., may contain repeating patterns of DPTT values) that may be analyzed to derive a measure of respiratory effort. In one suitable approach, multiparameter patient monitor 26 may be configured to display plots 510, 520, 600, and/or 700.

From these DPTT measurements, reliable and accurate blood pressure values may be computed on a continuous or periodic basis, as will be described below. In an embodiment, the changes in blood pressure directly correlate to the respiratory effort of a patient. For example, a patient's change in blood pressure may be taken as a change in the respiratory effort of the patient. Thus, the changes in DPTT over time may be used to determine relative changes in respiratory effort. In an example, the change in blood pressure over a respiratory cycle may be determined based on characteristic measurements (e.g., maximum and minimum measurements) of DPTT during that respiratory cycle. In turn, the respiratory effort may be determined to be directly correlated to these changes in DPTT—for example, the larger difference between the maximum and minimum DPTT during the respiratory cycle, the higher the measurement of respiratory effort. In another example, the mean DPTT value over a period of time may be used to determine a change in blood pressure—for example, a larger mean DPTT value over a first period of time may correlate to a blood pressure measurement that is lower relative to an initial blood pressure measurement. In turn, the respiratory effort of a patient during the first period of time may be determined to be higher than during the period of time associated with the initial blood pressure measurement.

Focusing now on plots 510 and 520 of FIGS. 5(a) and 5(b), in order to calculate respiratory effort from DPTT measurements, values of signals 505 and 525 may be selected. This selection may be based on identified characteristic points (e.g., maximum, minimum) for blood pressure calculations. These calculations may include, for example, taking a natural logarithm of a time difference between two characteristic points, or by solving a multi-parameter equation, such as $p=a+b \cdot \ln(T)$, or a mathematical equivalent thereof, where p is the determined blood pressure measurement, T is a time difference determined from the identified characteristic points, and a and b are constants.

In an embodiment, a multi-parameter equation (i.e., equation (1)) may be adopted to calculate the difference between two readings of DPTT such that no blood pressure calibrations need be performed—i.e., the blood pressure calculation is performed using only the DPTT readings. For example, the multi-parameter equation may be adopted for two readings of DPTT taken at two different times—e.g., $$P_0 = a + b \cdot \ln(T_0)$$

and $$P_1 = a + b \cdot \ln(T_1) \qquad (6),$$

where $P_0$ and $P_1$ are relative blood pressure measurements, $T_0$ and $T_1$ are DPTTs determined from the identified characteristic points, a is a constant, and b is proportional to the times $T_0$ and $T_1$. Accordingly, the change in pressure may be calculated as $$\Delta P = b \cdot (\ln(T_0) - \ln(T_1)) \quad (7).$$

In an embodiment, $b = c3 \cdot T + c4$, where T is the average of $T_0$ and $T_1$, and c3 and c4 are pressure constants. In such embodiments, the equation for change in blood pressure may be rewritten as $$\Delta P = (c_3 \cdot ((T_0 + T_1)/2) + c_4) \cdot (\ln(T_0) - \ln(T_1)) \quad (8).$$

In other embodiments, T may be any other suitable DPTT's that may, for example, be proportional to $T_0$ and $T_1$, including the values of $T_0$ and $T_1$ themselves.

In an embodiment, the identified DPTTs of characteristic points used in blood pressure calculation may be selected according to the maximum and minimum DPTT values throughout an entire respiration cycle. Exemplary respiration cycles are illustrated in portion 514 of signal 505 and portion 524 of signal 525. In an embodiment, a respiration cycle may be observed using a moving window of time of any suitable length—for example, 1, 1.5, 3, 5, or any suitable number of seconds. The maximum and minimum DPTT values may be selected over a respiratory cycle because of the stability and accuracy of such values as compared to the frequent and/or erratic localized oscillations in DPTT throughout a single cycle (e.g., the localized fluctuations illustrated in portion 514 of signal 505 and portion 524 of signal 525). In an embodiment, the maximum and minimum DPTT values within a respiration cycle may be determined using any suitable combination of signal processing techniques for determining fiducial points within a signal, including transformation, manipulation, and/or filtering techniques. Such techniques are described with respect to FIG. 3 and in, for example, U.S. patent application No. 61/369,452, filed Jul. 30, 2010, entitled "Systems and Methods for Processing Multiple Physiological Signals, which is hereby incorporated by reference herein in its entirety.

In an embodiment, changes in systolic and diastolic pressure may be calculated using the equation $$\Delta P = (c_3 \cdot ((T_0 + T_1)/2) + c_4) \cdot (\ln(T_0) - \ln(T_1)) \quad (9)$$

and substituting in different sets of constants for $c_3$ and c depending on whether systolic pressure or diastolic pressure is being calculated. For example, when a change in systolic pressure is calculated, $c_3$ may be set to 0.44 while $c_4$ is set to −9.1. In addition, when a change in diastolic pressure is calculated, $c_3$ may be set to −0.26 while $c_4$ is set to −4.4. In an embodiment, constants $c_3$ and $c_4$ may be selected separate from any blood pressure calibration reading. For example, with reference to FIG. 5A, signal 505 may be observed over portion 514. Using suitable signal processing techniques, the maximum systolic DPTT 511 may be determined to be 50.5 milliseconds, and a minimum systolic DPTT 513 may be determined to be 40 milliseconds. Applying these measurements to the equation for $\Delta P$ with $c_3$ set to 0.44 and $c_4$ set to −9.1, the change in systolic blood pressure is calculated to be 6.76 mmHg. Similarly, with reference to FIG. 5B, signal 525 may be observed over portion 524. Using suitable signal processing techniques, the maximum diastolic DPTT 521 may be determined to be 55.5 milliseconds, and a minimum diastolic DPTT 523 may be determined to be 49.5 milliseconds. Applying these measurements to the equation for $\Delta P$ with $c_3$ set to −0.26 and $c_4$ set to −4.4, the change in diastolic blood pressure is calculated to be 2.06 mmHg. In an embodiment (not shown), identified characteristic points $T_0$ and $T_1$ used in blood pressure calculation may be selected according to the maximum and minimum DPTT values of a DPTT signal associated with thoracic DPTT measurements. Changes in thoracic blood pressure may be calculated using the equation (9) in a manner similar to the calculation described with respect to systolic and diastolic blood pressure above using the constants $c_3$ and $c_4$. The constants may be further optimized for the changes in thoracic pressure associated with respiratory effort derived from empirical data.

In an embodiment, the change in blood pressure calculated using equation (9) directly correlates to the respiratory effort of a patient. Thus, the changes in DPTT over a respiratory cycle may be used to determine relative changes in respiratory effort. In an example, the change in respiratory effort may be calculated based on a change in blood pressure calculated according to the maximum and minimum DPTT values selected throughout a respiration cycle. For example, a higher measurement of respiratory effort may be calculated the larger the difference the between the maximum and minimum DPTT during the respiratory cycle. The maximum and minimum DPTT values may be selected according to the methods discussed FIGS. 5(a) and 5(b).

In an embodiment, the window in which maximum and minimum DPTT measurements are taken may be reduced in size (e.g., from 3 seconds to 1.5 seconds) such that the respiration modulation can be better observed in the signal. In addition, the resolution of signals 505 and 525 may be increased (e.g., by increasing the reducing the reporting increment from 0.4 seconds to 0.1 seconds) to allow for a higher resolution of respiratory modulations.

In an embodiment, calculated changes in diastolic and systolic blood pressure measurements may be used in combination to obtain a change in MAP. The MAP may be calculated according to a weighted average of contemporaneous changes in diastolic, systolic, and/or thoracic pressure. For example, the change in mean arterial pressure may be calculated according to $$\Delta P_{map} = (\Delta P_{sys} + 2\Delta P_{dia})/3 \quad (10),$$

where $\Delta P_{sys}$ and $\Delta P_{dia}$ are contemporaneous changes in systolic and diastolic pressures, respectively. For example, if the change in systolic pressure is 6.76 mmHg and the change in diastolic pressure is 2.06 mmgH, the change in the MAP according to equation (10) would be 3.63 mmHg. In an embodiment, the MAP may be calculated based on a weighted average of contemporaneous changes in diastolic and thoracic pressure, systolic and thoracic pressure, or diastolic, systolic, and thoracic pressure. In an embodiment, the MAP may be calculated separate from any blood pressure calibration reading.

In an embodiment, the change in MAP calculated using equation (10) directly correlates to the respiratory effort of a patient. Thus, a weighted average of the changes in diastolic, systolic, and/or thoracic DPTT over a period of time may be used to determine relative changes in respiratory effort. In an example, the change in respiratory effort may be calculated based on a change in MAP, which includes a weighted average of the changes in diastolic and systolic blood pressures over a respiratory cycle. As discussed, this calculation of respiratory effort does not require calibration readings from a non-invasive blood pressure cuff.

Figure 6:
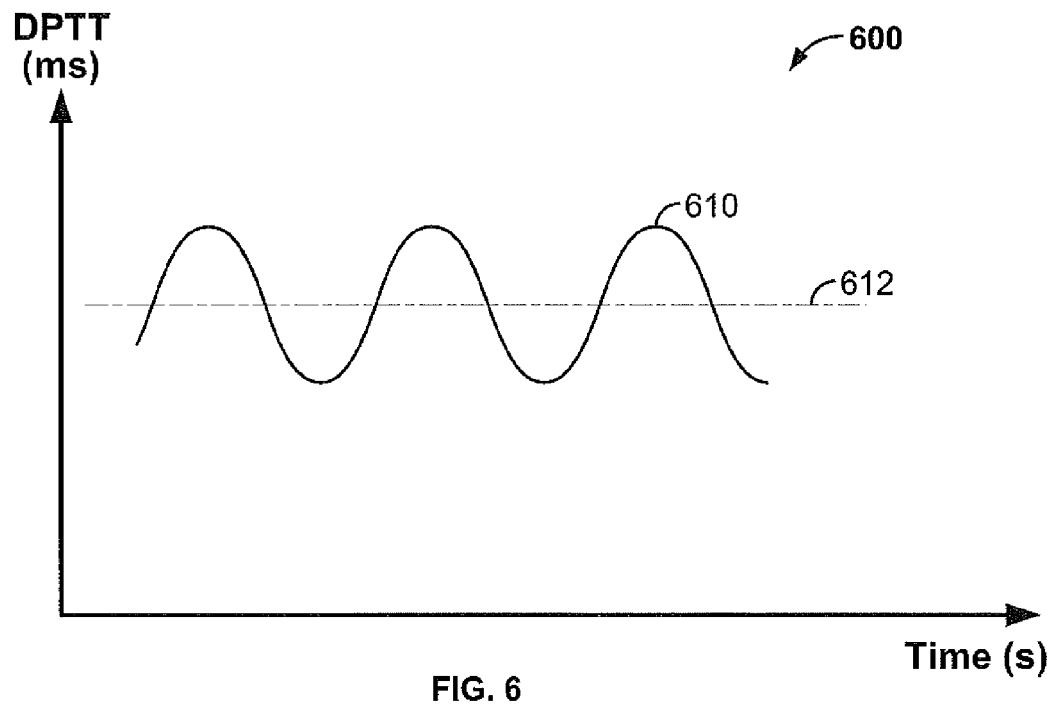
FIG. 6 shows an illustrative plot of a mean DPTT measurement over a first period of time in accordance with an embodiment.

FIG. 6 shows an illustrative plot 600 of a mean DPTT measurement 612 associated with DPTT signal 610 over a first period of time in accordance with an embodiment of the disclosure. As mentioned above, DPTT signal 610 may be representative of either systolic or diastolic DPTT measurements. In an embodiment, mean DPTT measurement 612 may be calculated using any suitable signal processing techniques, including, for example, any suitable filtering techniques such as low-pass filtering. The mean DPTT measurement 612 may be used to calculate a change in blood pressure along any point in DPTT signal 610, (i.e., a running value of the fluctuation in systolic or diastolic pressure). For example, a running value of the fluctuation in systolic or diastolic pressure may be calculated according to $$\Delta P = (c_3 \cdot T_m + c_4) \cdot (\ln(T) - \ln(T_m)) \quad (11)$$

where T is any point along a DPTT signal (e.g., DPTT signal 610), $T_m$ is the mean DPTT measurement associated with the DPTT signal, and $c_3$ and $c_4$ are pressure constants associated with calculation of changes in diastolic or systolic pressure (e.g., the pressure constants discussed above with respect to FIGS. 5A and 5B). In this manner, a highly localized change in blood pressure may be obtained. In an embodiment, the fluctuation in systolic or diastolic pressure calculated in equation (11) directly correlates to the respiratory effort of a patient. For example, the blood pressure variation given by equation 11 may be taken as the respiratory effort of the patient.

Figure 7:
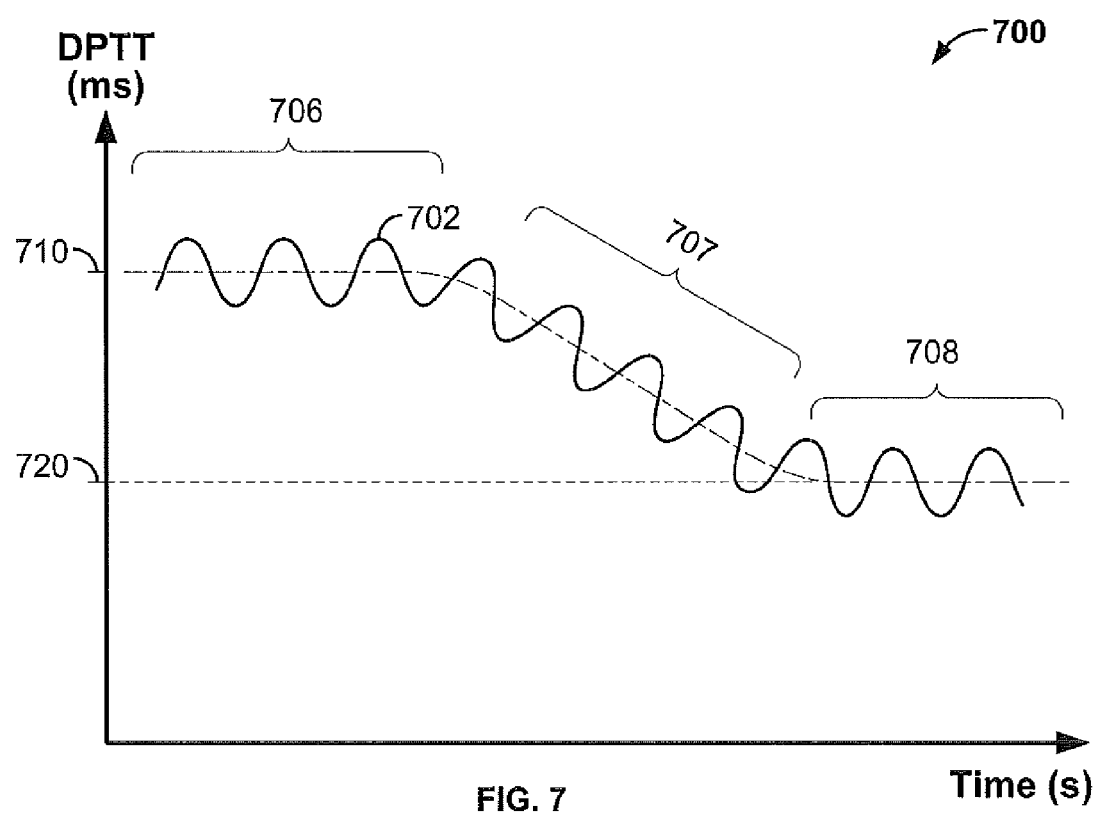
FIG. 7 shows an illustrative plot of mean DPTT measurements over multiple periods of time in accordance with an embodiment of the disclosure.

FIG. 7 shows an illustrative plot 700 of mean DPTT measurements 710 and 720 over multiple periods of time associated with a DPTT signal 702 in accordance with an embodiment of the disclosure. In an embodiment, the equations discussed with respect to FIGS. 5(*a*), 5(*b*), and 6 may be adopted to calculate localized blood pressure changes other than those associated with a single respiratory cycle (e.g., those changes discussed with respect to FIGS. 5(*a*) and 5(*b*)) or highly localized fluctuations (e.g., those changes discussed with respect to FIG. 6). These changes in pressure may occur over short periods of respiratory activity, (e.g. seconds), or longer periods, (e.g. several seconds or minutes). For example, as illustrated in FIG. 7, a patient may be breathing normally during first period of respiratory activity 706, transition into a period of restricted breathing activity during second period of respiratory activity 707, and sustain a period of restricted breathing activity during third period of respiratory activity 708. The transition into and duration of the period of restricted breathing activity may be due to increased autonomic and/or respiratory activity on behalf of the patient being monitored—for example, sitting up on a bed or walking on a treadmill. In an embodiment, DPTT signal 702 may change in baseline (i.e., mean DPTT) or amplitude during this increased autonomic activity. For example, mean DPTT measurement 720 associated with signal 702 during third time period 708 may be lower than mean DPTT measurement 710 associated with signal 702 during first time period 706. In addition, the amplitude of signal 702 may be larger during third time period 708 than during first time period 706.

In an embodiment, mean DPTT values may be calculated for several time periods of signal 702. For example, separate mean DPTT values may be calculated for first time period 706, second time period 707, and third time period 708. These mean DPTT values may then be used to calculate localized changes in pressure due to increased autonomic activity. In an embodiment, this localized change in blood pressure may be calculated during time periods in which the mean DPTT is stable for a suitable threshold amount of time. For example, the localized change in blood pressure may be calculated as:

$$\Delta P_{loc} = (c_3 \cdot ((T_{m3} + T_{m4})/2) + c_4) \cdot (\ln(T_{m3}) - \ln(T_{m4})) \quad (12)$$

Where $T_{m3}$ is the mean DPTT value of a first time period in which the mean DPTT was stable (e.g., first time period 706), $T_{m4}$ is the mean DPTT value of a second time period in which the mean DPTT was stable (e.g., third time period 708), and $c_3$ and $c_4$ are pressure constants associated with calculation of changes in diastolic or systolic pressure (e.g., the pressure constants discussed above with respect to FIGS. 5A and 5B). In this manner, a change in blood pressure may be calculated according to the changes in baseline of signal 702 rather than changes in amplitude. In one suitable approach, mean DPTT values may be calculated for several time periods of several DPTT signals, and then used to calculate localized changes in pressure according to equation (12) above.

In an embodiment, the change in blood pressure calculated using equation (12) directly correlates to the respiratory effort of a patient. Thus, the changes in mean DPTT over periods of time may be used to determine relative changes in respiratory effort.

In an embodiment, it will be understood that the calculation of changes in systolic and/or diastolic blood pressure described with respect to FIGS. 5(*a*), 5(*b*), 6, and 7 need not depend on any blood pressure calibration reading. Further, in an embodiment, it will be understood that changes in blood pressure may be determined according to the calculations described with respect FIGS. 5(*a*), 5(*b*), 6, and 7 using any suitable relationship between pressure and changes in DPTT—such as a relationship other than the logarithmic relationship established in the equations discussed above, (e.g., a linear relationship).

Figure 8:
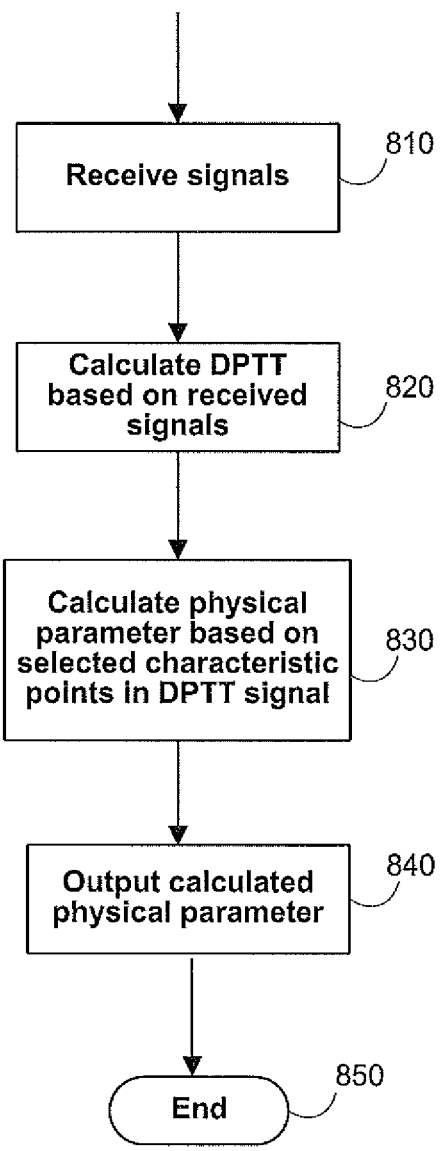
FIG. 8 is a flowchart of an illustrative process for computing a physical parameter based on a localized change in DPTT in accordance with an embodiment.

FIG. 8 is a flowchart 800 of illustrative steps for computing a physical parameter based on a localized change in DPTT in accordance with an embodiment of the disclosure. Flow chart 800 may be performed by processor 412 (FIG. 4) or microprocessor 48 (FIG. 2) in real time using a PPG signal obtained by sensor 12 (FIG. 2) or input signal generator 410 (FIG. 4), which may be coupled to patient 40, using a time window smaller than the entire time window over which the PPG signal may be collected. Alternatively, flow chart 800 may be performed offline on PPG signal samples from QSM 72 (FIG. 2) or from PPG signal samples stored in RAM 54 or ROM 52 (FIG. 2), using the entire time window of data over which the PPG signal was collected.

Process 800 may begin at step 810, in which PPG signals may be collected by sensor 12 or input signal generator 410 over any suitable time period t to compute changes in physical parameters. In an embodiment, PPG signals may be collected corresponding to sensors located at different distances from the heart (e.g., at the finger and forehead). These signals may include a baseline signal that may fluctuate due to the breathing of patient 40, which may cause the PPG signals to oscillate, or twist, in the time plane. For example, the PPG signals may experience amplitude modulation that may be related to dilation of the patient's vessels in correspondence with the patient's respiration. In addition, the PPG signals may experience baseline modulation that may be related to the breathing effort of the patient in correspondence to breathing restrictions or stresses placed on the patient (e.g., exercise). At step 820, DPTT signals may be calculated based on the signals received at step 810. In an embodiment, separate DPTT signals may be calculated to reflect diastolic and systolic periods of respiration. The DPTT signals may be calculated using any suitable combination of signal processing techniques, such as performing a maximum correlation algorithm based on derivatives calculated from the PPG signals, and/or using a degree of confidence calculation. Such techniques are further described in U.S. patent application Ser. No. 12/847,546, filed Jul. 30, 2010, entitled "Systems and Methods for Improved Computation of Differential Pulse Transit Time from Photoplethysmograph Signals, which is hereby incorporated by reference herein in its entirety. In an embodiment, the resolution of the calculated DPTT signals may be increased (e.g., by increasing the reducing the reporting increment from 0.4 seconds to 0.1 seconds) to allow for a higher resolution of respiratory modulations.

At step 830, localized changes in physical parameters may be calculated based on selected characteristic points in the DPTT signals. In an embodiment, the characteristic points may be selected according to the desired type of localized change in the physical parameter. For example, localized changes in diastolic or systolic blood pressure may be calculated according to selected maximum and minimum points within a windowed portion of the DPTT signals by using equation (9). The windowed portion may correspond to a single respiratory cycle of patient 40. In an embodiment, separate calculations may be performed using diastolic and systolic DPTT signals to determine changes in diastolic and systolic pressure. In an embodiment, both diastolic and systolic DPTT signals may be used to calculate a MΔP (e.g., by using equation (10)). A fluctuation in blood pressure may be calculated using any selected point in the DPTT signal along with a mean DPTT value associated with the DPTT signal (e.g., by using equation (11)). Other localized blood pressure changes may be calculated using several mean DPTT values from different portions of DPTT signals (e.g., a portion where patient 40 is resting and a portion where patient 40 is exercising) by using equation (12). After a blood pressure measurement is determined at step 830, process 800 may repeat step 830 using different characteristic points to calculate different changes in blood pressure. As such, process 800 may generate blood pressure measurements continuously. In an embodiment, the calculated change in blood pressure may be independent from any blood pressure calibration, as the only parameters used to calculate blood pressure from the patient are derived from DPTT signals themselves. In an embodiment, the calculated change in blood pressure may be in absolute units of pressure (e.g., mmHG or $cmH_2O$). In an embodiment, the calculated changes in blood pressure directly correlate to the respiratory effort of a patient. Thus, the calculated changes in blood pressure may be used to calculate relative changes in respiratory effort. In an embodiment, the calculated changes in blood pressure may be taken to be the respiratory effort of a patient. Step 830 is described in greater detail with respect to the steps of process 900 of FIG. 9 below.

At step 840, the calculated physical parameter may be output in any suitable fashion, for example by storing or displaying the calculated physical parameter. For example, multi-parameter patient monitor 26 (FIG. 1) may display a patient's blood pressure on display 28 (FIG. 1). Additionally or alternatively, the measurements may be saved to memory or a storage device (e.g., ROM 52 or RAM 54 of monitor 14 (FIG. 2)) for later analysis or as a log of a patient's medical history. Process 800 may then proceed to step 850 and end.

Figure 9:
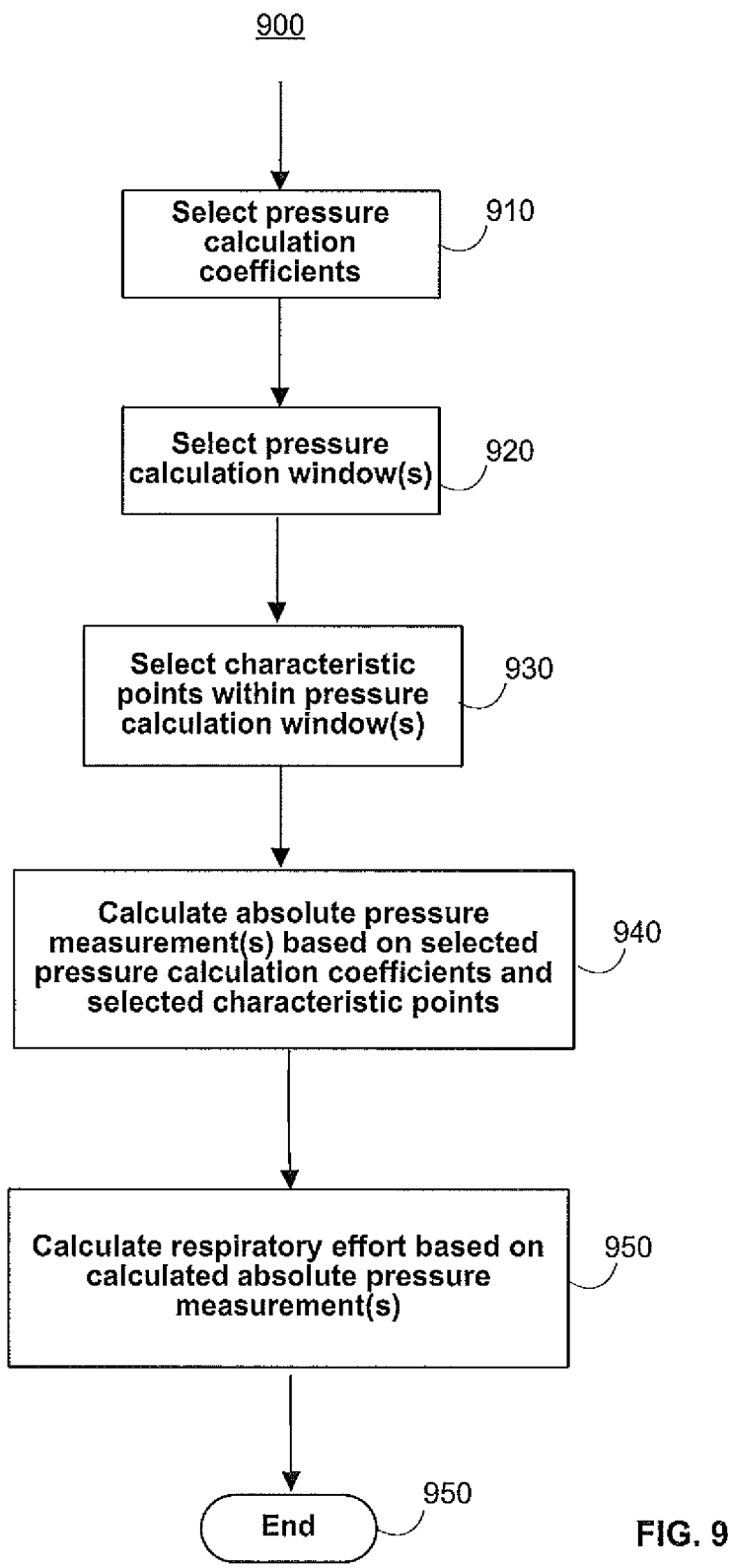
FIG. 9 is a flowchart of an illustrative process for computing an absolute blood pressure measurement based on a localized change in DPTT in accordance with an embodiment.

FIG. 9 is a flowchart 900 of illustrative steps for computing an absolute pressure measurement based on a localized change in DPTT in accordance with an embodiment of the disclosure. In an embodiment, the steps of process 900 may be executed as part of step 830 of process 800 (FIG. 8). Process 900 may be performed by processor 412 (FIG. 4) or microprocessor 48 (FIG. 2) substantially similarly to process 800. Process 900 may begin at step 910. At step 910, pressure calculation coefficients may be selected for use in the computation of absolute blood pressure. In an embodiment, the pressure calculation coefficients may be selected according to the desired type of pressure calculation and/or the DPTT signals available for pressure calculation (e.g., the DPTT signals calculated at step 820 by processor 412 (FIG. 4) or microprocessor 48 (FIG. 2)). For example, the pressure calculation coefficients may be selected based on whether the desired pressure calculation is a diastolic, systolic, or thoracic blood pressure measurement, and/or whether the available DPTT signals are associated with DPTT measurements from diastolic, systolic, or thoracic periods of a heart beat. Suitable pressure calculation coefficients for systolic and diastolic blood pressure calculation may be substantially similar to the pressure constants discussed with respect to equation (9) as well as FIGS. 5A and 5B.

At step 920, a window, or portion, of the DPTT signals available for pressure calculation may be selected for use in the computation of absolute blood pressure. In an embodiment, the window may be selected according to the desired degree of localization of the computation of absolute blood pressure. For example, if the desired degree of localization of the blood pressure measurement is an entire respiration cycle, the window may be selected as a portion of the DPTT signal that reflects an entire respiration cycle, such as portion 514 (FIG. 5A). As another example, if the desired degree of localization of the blood pressure measurement is high, the window may be selected to be an infinitesimal slice of the DPTT signal, such as a collection of points of the DPTT signal. Finally, if the desired degree of localization of the blood pressure measurement is low, the window may be selected to be a portion of the DPTT signal that reflects several respiration cycles, such as 2, 3, 5, 10, or any number of suitable respiration cycles. In an embodiment, several discontinuous portions of the available DPTT signals may be selected for the blood pressure calculation window such that there are multiple blood pressure calculation windows.

At step 930, characteristic points of the DPTT signal may be selected within the blood pressure calculation windows for use in the computation of absolute blood pressure. In an embodiment, the characteristic points may be selected based on distinguishing features of the selected portions of the DPTT signals, such as maximum, minimum, or mean DPTT values within the blood pressure calculation window. These characteristic points may be useful in the calculation of blood pressure according to equation (9) or (10). In an embodiment, the characteristic points may be calculated based on a mean value of a portion of the points of the DPTT signal within the blood pressure calculation window. These characteristic points may be useful in the calculation of blood pressure according to equation (11). In an embodiment, the characteristic points may be selected based on a desired localized change in blood pressure—e.g., at a point in which the baseline of the DPTT signal is stable, such as when the patient is in a state of exercise or in a state of rest, but not in transition between the two. These characteristic points may be useful in the calculation of blood pressure according to equation (12).

At step 940, an absolute blood pressure measurement is calculated based on the pressure calculation coefficients selected at step 910 and the characteristic points selected at step 930. These calculations may be performed according to equations (9) through (12) substantially similar to the calculations described with respect to step 830. After a blood pressure measurement is determined at step 940, process 900 may repeat steps 810, 820, and 830, to select different pressure coefficients and characteristic points to calculate different changes in blood pressure. As such, process 900 may generate blood pressure measurements continuously. In an embodiment, the calculated change in blood pressure may be independent from any blood pressure calibration, as the only parameters used to calculate blood pressure from the patient are derived from DPTT signals themselves.

At step 950, respiratory effort is calculated based on the absolute blood pressure measurements calculated at step 940. These calculations may be based on, for example, a direct correlation between blood pressure and respiratory effort (e.g., those correlations discussed with respect to FIGS. 5(*a*), 5(*b*), 6, and 7. In an example, a higher measurement of respiratory effort may be calculated the larger the difference the between the maximum and minimum DPTT during the respiratory cycle. In addition, a higher measurement of respiratory effort may be calculated the larger the difference between a lower mean DPTT value over a first period of time as compared to a higher mean DPTT value over a second period of time. In an embodiment, the calculated changes in blood pressure may be taken to be the respiratory effort of a patient.

In practice, one or more steps of processes 800 and 900 may be combined with other steps, performed in any suitable order, performed in parallel (e.g., simultaneously or substantially simultaneously), or removed.

The foregoing is merely illustrative of the principles of this disclosure and various modifications can be made by those skilled in the art without departing from the scope and spirit of the disclosure. The above described embodiments are presented for purposes of illustration and not of limitation. The present disclosure also can take many forms other than those explicitly described herein. Accordingly, it is emphasized that the disclosure is not limited to the explicitly disclosed methods, systems, and apparatuses, but is intended to include variations to and modifications thereof which are within the spirit of the following claims.

What is claimed is:

1. A method for calculating a measure of respiratory effort of a subject, the method comprising:
   receiving two photoplethysmograph (PPG) signals corresponding to two different locations on the subject;
   calculating, using electronic processing equipment, differential pulse transit time (DPTT) values for the two PPG signals, wherein the DPTT values represent differences in arrival times between the two locations;
   determining, using the electronic processing equipment, a measure of respiratory effort based at least in part on the calculated DPTT values; and
   storing, using a storage device, the measure of respiratory effort.

2. The method of claim 1, wherein the determining further comprises:
   selecting a plurality of pressure calculation coefficients based on the calculated DPTT values;
   selecting a plurality of characteristic DPTT values;
   determining, based at least in part on the selected pressure calculation coefficients and selected characteristic DPTT values, a measure of blood pressure; and
   calculating, based at least in part on the measure of blood pressure, a measure of respiratory effort.

3. The method of claim 2, wherein the measure of blood pressure is determined solely based on the selected pressure calculation coefficients and selected characteristic DPTT values.

4. The method of claim 2, further comprising:
   selecting at least a portion of the calculated DPTT values corresponding to at least one respiratory cycle of the subject; and
   selecting a plurality of characteristic DPTT values within the portion of the DPTT values.

5. The method of claim 4, wherein the characteristic DPTT values are selected based on at least a maximum DPTT value and a minimum DPTT value in the portion of the DPTT values.

6. The method of claim 4, further comprising calculating a mean DPTT value corresponding to the at least one respiratory cycle of the subject.

7. The method of claim 2, further comprising:
   selecting at least a portion of the calculated DPTT values corresponding to at least two periods of respiratory activity;
   calculating a mean DPTT value corresponding to each of the at least two periods of respiratory activity; and
   determining, based at least in part on the selected pressure calculation coefficients and calculated mean DPTT values, the measure of blood pressure.

8. The method of claim 7, wherein the at least two periods of respiratory activity correspond to at least one period in which the subject is exercising and at least one period in which the subject is resting.

9. The method of claim 1, wherein the calculation of the measure of respiratory effort is based on a linear relationship between a measure of blood pressure and respiratory effort.

10. A system for calculating a measure of respiratory effort of a subject, comprising:
    an input for receiving two photoplethysmograph (PPG) signals corresponding to two different locations on the subject;
    a processor configured to use at least portions of the two PPG signals to:
       calculate differential pulse transit time (DPTT) values for the two PPG signals, wherein the DPTT values represent differences in arrival times between the two locations; and
       determine a measure of respiratory effort based at least in part on the calculated DPTT values; and
    a storage device for storing the measure of respiratory effort.

11. The system of claim 10, wherein the processor is configured to use at least a portion of the calculated DPTT values to:
    select a plurality of pressure calculation coefficients based on the calculated DPTT values;
    select a plurality of characteristic DPTT values;
    determine, based at least in part on the selected pressure calculation coefficients and selected characteristic DPTT values, a measure of blood pressure; and
    calculate, based at least in part on the measure of blood pressure, a measure of respiratory effort.

12. The system of claim 11, wherein the measure of blood pressure is determined solely based on the selected pressure calculation coefficients and selected characteristic DPTT values.

13. The system of claim 11, wherein the processor is configured to use at least a portion of the calculated DPTT values to:
    select at least a portion of the calculated DPTT values corresponding to at least one respiratory cycle of the subject; and
    select a plurality of characteristic DPTT values within the portion of the DPTT values.

14. The system of claim 13, wherein the characteristic DPTT values are selected based on at least a maximum DPTT value and a minimum DPTT value in the portion of the DPTT values.

15. The system of claim 13, wherein the processor is further configured to calculate a mean DPTT value corresponding to the at least one respiratory cycle of the subject.

16. The system of claim 11, wherein the processor is configured to use at least a portion of the calculated DPTT values to:
    select at least a portion of the calculated DPTT values corresponding to at least two periods of respiratory activity;
    calculate a mean DPTT value corresponding to each of the at least two periods of respiratory activity; and determine, based at least in part on the selected pressure calculation coefficients and calculated mean DPTT values, the measure of blood pressure.

17. The system of claim 16, wherein the at least two periods of respiratory activity correspond to at least one period in which the subject is exercising and at least one period in which the subject is resting.

18. The system of claim 10, wherein the calculation of the measure of respiratory effort is based on a linear relationship between a measure of blood pressure and respiratory effort.

19. Non-Transitory computer readable storage media comprising instructions for:
   receiving two photoplethysmograph (PPG) signals corresponding to two different locations on the subject;
   calculating differential pulse transit time (DPTT) values for the two PPG signals, wherein the DPTT values represent differences in arrival times between the two locations;
   determining a measure of respiratory effort based at least in part on the calculated DPTT values; and
   storing the measure of respiratory effort.

* * * * *